US 7,177,533 B2

(12) United States Patent
McFarlin et al.

(10) Patent No.: US 7,177,533 B2
(45) Date of Patent: Feb. 13, 2007

(54) MOTOR CONTROL SYSTEM FOR A SURGICAL HANDPIECE

(75) Inventors: Kevin L. McFarlin, Jacksonville, FL (US); Cecil O. Lewis, Jacksonville, FL (US)

(73) Assignee: Medtronic, Inc., Minneapolis, MN (US)

( * ) Notice: Subject to any disclaimer, the term of this patent is extended or adjusted under 35 U.S.C. 154(b) by 1035 days.

(21) Appl. No.: 09/961,760

(22) Filed: Sep. 24, 2001

(65) Prior Publication Data

US 2002/0038102 A1   Mar. 28, 2002

Related U.S. Application Data

(60) Provisional application No. 60/235,217, filed on Sep. 24, 2000.

(51) Int. Cl.
*H02P 5/00* (2006.01)

(52) U.S. Cl. .................. 388/800; 388/937; 388/935; 318/432; 318/434; 606/167; 606/170

(58) Field of Classification Search .............. 388/937, 388/935, 800; 318/432, 434; 606/162, 170
See application file for complete search history.

(56) References Cited

U.S. PATENT DOCUMENTS

| 4,230,977 A | 10/1980 | Nelson |
| 4,705,038 A * | 11/1987 | Sjostrom et al. ........... 606/180 |
| 5,455,766 A | 10/1995 | Scheller et al. |
| 5,543,695 A | 8/1996 | Culp et al. |
| 5,563,481 A | 10/1996 | Krause |
| 5,602,449 A | 2/1997 | Krause et al. |
| 5,672,945 A | 9/1997 | Krause |
| 5,689,159 A | 11/1997 | Culp et al. |
| 5,712,543 A * | 1/1998 | Sjostrom .................... 318/71 |
| 5,788,688 A * | 8/1998 | Bauer et al. ................... 606/1 |
| 5,804,936 A | 9/1998 | Brodsky et al. |
| 5,903,117 A * | 5/1999 | Gregory .................... 318/254 |
| 5,910,152 A | 6/1999 | Bays |
| 5,921,956 A * | 7/1999 | Grinberg et al. ......... 604/95.01 |
| 5,957,945 A | 9/1999 | Bays |
| 5,964,746 A * | 10/1999 | McCary ........................ 606/1 |
| 6,017,354 A * | 1/2000 | Culp et al. .................. 606/170 |
| 6,037,724 A | 3/2000 | Buss et al. |
| 6,050,989 A | 4/2000 | Fox et al. |
| 6,090,123 A | 7/2000 | Culp et al. |
| 6,245,084 B1 * | 6/2001 | Mark et al. ................. 606/167 |

FOREIGN PATENT DOCUMENTS

| EP | 0 890 343 A2 | 1/1999 |
| WO | WO 00/23020 | 4/2000 |

\* cited by examiner

*Primary Examiner*—Rina Duda
(74) *Attorney, Agent, or Firm*—Dicke, Billig & Czaia, PLLC

(57) ABSTRACT

A system and method for powered surgical handpiece capable of powering various micro-cutting instruments is described. The system is comprised of a controller adapted for controlling/interfacing with a powered surgical handpiece based upon user-defined procedural information. A data entry device is used for entering the user-defined procedural information used by the controller for configuring and operating the motor control system.

19 Claims, 6 Drawing Sheets

MOTOR CONTROL SYSTEM FOR A SURGICAL HANDPIECE

CROSS-REFERENCE TO RELATED APPLICATION

This application claims the benefit of, and incorporates herein by reference the entirety of, U.S. Provisional Application Ser. No. 60/235,217, filed on Sep. 24, 2000.

BACKGROUND OF THE INVENTION

The present invention generally relates to powered handpieces for driving surgical cutting instruments. More particularly, it relates to a control system for interfacing with a powered surgical handpiece and controlling operation thereof.

Powered surgical handpieces are commonly used in many medical specialties to drive surgical blades or cutting instruments for performing various diverse cutting functions including resection, comminution, dissection, debridement, shaving, drilling, pulverizing, and shaping of anatomical tissue. In the areas of ENT/head/neck surgery, the handpieces are typically configured for selective coupling to, and driving of, a variety of different micro-cutting surgical instrument design to perform a specific procedure. During use, based upon the specific surgical procedure, the surgeon selects the appropriate micro-cutting tool and mounts it to the powered handpiece. The powered handpiece is then operated to move one or more components of the micro-cutting tool (e.g., rotation, oscillation) required to perform the surgical operation. As a point of reference, the rotational requirements typically required by a powered surgical handpiece for ENT/head/neck procedures range from about 500 rpm for a laryngeal skimming operations to in excess of 60,000 rpm for high-speed drill operations. The common speed range of the powered surgical handpiece is from about 300 rpm to about 80,000 rpm.

In addition to motor improvements, such as use of brushless DC motors, overall systems have been developed for use with the powered surgical handpiece and related surgical micro-cutting instruments. A typical system, in addition to a powered handpiece and one or more micro-cutting instruments, includes a control console and a cable that connects the handpiece to the console. The control console is configured to activate and/or control energization of the motor otherwise associated with the powered surgical handpiece. For example, a hand or foot switch can be provided as part of the system. Depending upon the surgeon's manipulation of the foot or hand switch, a corresponding signal is delivered to the control console that, in turn, energizes the handpiece to a corresponding speed.

The improved capabilities of powered surgical handpieces, as well as the vast number of available surgical micro-cutting instruments now available, have undoubtedly greatly increased the number of ENT/head/neck procedures that a surgeon can perform utilizing a single surgical system. However, with the substantial expansion in available procedures, the opportunity for improper device selection and/or operation has arisen. That is to say, because a surgeon can now use a single handpiece with a variety of different micro-cutting instruments to perform a number of different procedures, it is possible that surgical personnel may inadvertently operate the handpiece at settings that are less than optimal for a particular surgical procedure. For example, a surgeon performing a laryngeal tricut procedure with a micro-resecting instrument may accidentally attempt to operate the powered handpiece at speeds well in excess of the recommended 1,200 rpm limit because the surgeon has failed to adjust the control panel settings from a previous, different procedure; surgical personnel have been unable to recall the preferred settings, etc. Other operational settings, such as rotational mode (e.g., forward, reverse, oscillate), irrigation settings, etc., must also be determined and properly implemented by the surgical personnel, again increasing the opportunity for error.

Powered surgical handpieces, and in particular, powered handpieces configured to selectively receive a multitude of different micro-cutting instruments useful for ENT/head/neck surgeries, are highly desirable. However, the enhancement of available features may give rise to unintentional misoperation. Therefore, a need exists for an interactive powered surgical handpiece control system that controls surgical handpiece operation while providing information, assistance and/or control to the surgeon specific to a particular surgical operation.

SUMMARY OF THE INVENTION

One aspect of the present invention provides a motor control system for a powered surgical handpiece capable of powering various micro-cutting instruments. A controller is adapted for controlling/interfacing with a powered surgical handpiece based upon user-defined procedural information. A data entry device enables allows entry of user-defined procedural information used by the controller for configuring and operating the motor control system.

Another aspect of the present invention provides a surgical micro-cutting system. A surgical micro-cutting is used for performing diverse cutting functions. A powered surgical handpiece is configured to receive and drive the surgical micro-cutting instrument. A controller that operates the surgical micro-cutting system according to user-defined procedural information.

Another aspect of the present invention provides a method of controlling a powered surgical handpiece. The system includes a controller, a control console and a powered surgical handpiece capable of powering a micro-cutting instrument. The system detects whether the powered surgical handpiece is connected to the controller. The controller is operated to determine whether the micro-cutting instrument has been coupled to the powered surgical handpiece. Information and operational characteristics associated with user-defined procedural information entered by a user via the control console are generated and preferred operational settings are displayed based upon the generated information and operational characteristics. The system powers the powered surgical handpiece according to the operational characteristics associated with the user-defined procedural information.

DESCRIPTION OF THE PREFERRED EMBODIMENTS

Figure 1:
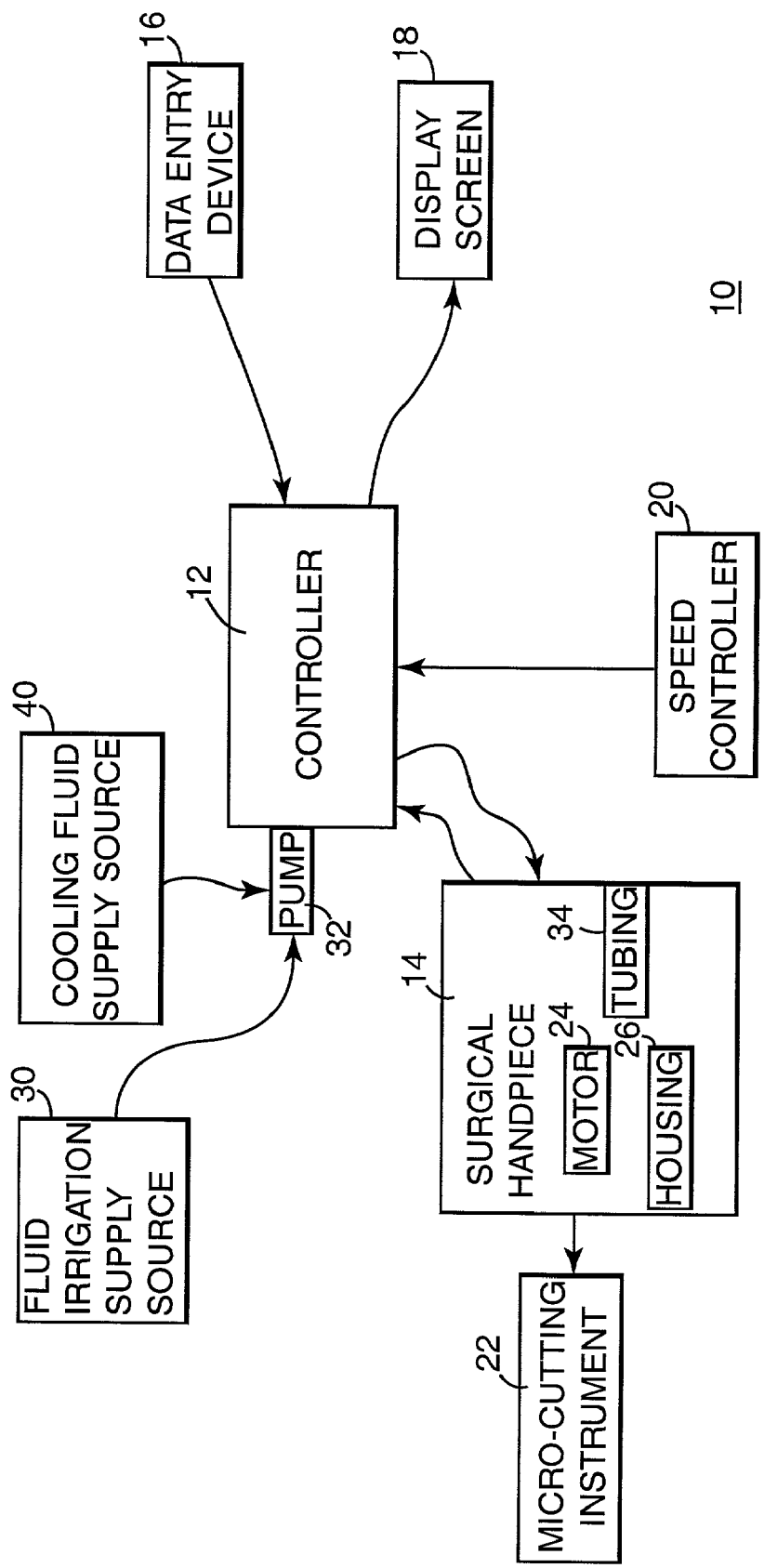
FIG. 1 is a block diagram of a powered surgical handpiece control system in accordance with the present invention.

One preferred embodiment of a powered surgical handpiece control system 10 is illustrated in block form in FIG. 1. The control system 10 includes a controller 12, a powered surgical handpiece 14, a data entry device 16, a display screen 18, and a speed controller 20. The various components of the control system 10 are described in greater detail below. In general terms, however, the handpiece 14, the data entry device 16, the display screen 18, and the speed controller 20 are electrically connected to the controller 12. During use, the controller 12 detects the presence of the powered handpiece 14, and receives procedural information from surgical personnel (not shown) via the data entry device 16. Based upon this information, the controller 12 displays operational information to the surgical personnel at the display screen 18. Depending upon the particular procedure to be performed, the controller 12 may request and receive additional procedural information from the surgical personnel via the data entry device 16 and/or display additional operational information at the display screen 18. Once the controller 12 has determined appropriate system configuration, the controller 12 energizes the handpiece 14 to a certain level that can be a default value, selected by the surgical personnel at the data entry device 16, dictated by operation of the speed controller 20, etc.

In a preferred embodiment, the controller 12, the data entry device 16, and the display screen 18 are provided in the form of a singular control console. In a preferred embodiment, the controller 12 is a microprocessor based computer including associated memory and associated input/output circuitry. Alternatively, a programmable logic controller (PLC) or other controller or equivalent circuitry can be employed.

The data entry device 16, which serves as a user interface, can assume a wide variety of configurations, and is preferably a membrane-type touch pad known in the art that is positioned in close proximity to, or integrally formed with, the display screen 18. Similarly, the display screen 18 can assume a wide variety of forms such as a cathode ray tube or a liquid crystal display. Regardless, the display screen 18 is configured to provide surgical personnel with information relating to operation of the system 10.

The powered surgical handpiece 14 is preferably of a type known in the art and is configured to selectively receive and drive a surgical micro-cutting instrument 22. Acceptable powered surgical handpieces are available, for example, from Medtronic-Xomed of Jacksonville, Fla., and include a motor 24 and housing 26. Examples of available powered surgical handpieces are described in U.S. Pat. Nos. 5,910, 152 and 5,957,881 the teachings of which are incorporated herein by reference, it being understood that those are but a few examples of acceptable powered surgical handpieces.

The surgical micro-cutting instrument 22 can assume a wide variety of forms as known in the art. For example, the micro-cutting instrument 22 can be a micro-resecting instrument, a micro-debriding instrument, a micro-shaving instrument, a micro-drilling instrument, a micro-abrasion instrument, etc. Regardless, the micro-cutting instrument 22 is configured for selectively coupling to, and driving by, the powered surgical handpiece 14.

As is known in the art, many ENT/head/neck microcutting procedures require a continuous supply of an irrigation fluid to the target site. For example, both micro-drilling and micro-shaving procedures require fluid irrigation. To this end, the system 10 preferably includes a separate irrigation fluid source 30 that is connected to the controller 12. With this configuration, the controller 12 controls activation of and/or the flow rate supplied to the target site. For example, in one preferred embodiment, the control system 10 includes, or is connected to, a pump 32 otherwise connected to the irrigation supply source 30. Upon activation by the controller 12, the pump 32 directs irrigation fluid to tubing 34 otherwise associated with the housing 26 of the handpiece 14. As is known in the art, the tubing 34 is preferably fluidly connected to a corresponding portion of the micro-cutting instrument 22 that otherwise directs the irrigation fluid to the target site. One example of an acceptable configuration is provided in U.S. Pat. No. 5,910,152. Alternatively, or in addition, the fluid irrigation supply source 30 can be directly connected to, or associated with, the handpiece 14, so that surgical personnel can directly control a supply of fluid.

Recent enhancements to powered handpiece designs have envisioned use of a liquid for cooling the powered handpiece 14 during use. In this regard, and in one preferred embodiment, the control system 10 further includes a cooling liquid supply source 40. As with the fluid irrigation supply source 30, described above, the cooling liquid supply source 40 can be directly connected to the handpiece 14 (e.g., the housing 26) for cooling thereof, or can be directed through, or controlled by, the controller 12.

Figure 2:
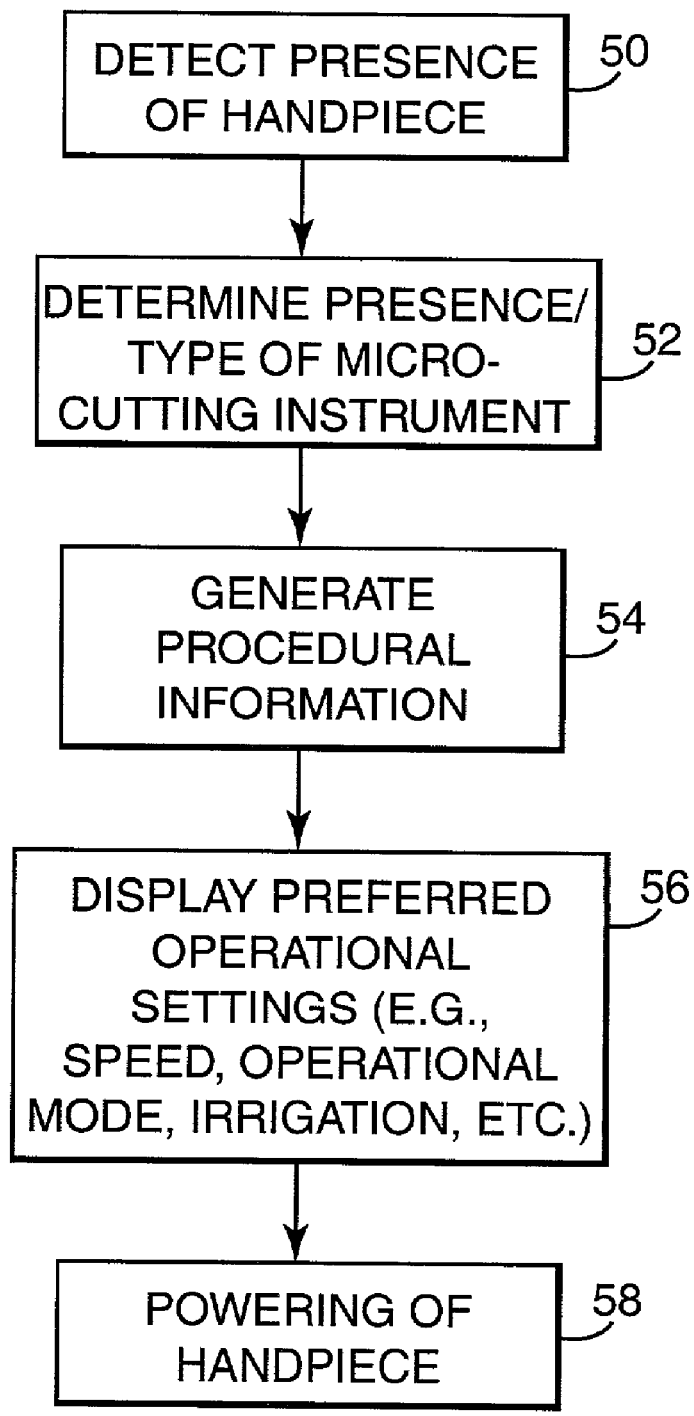
FIG. 2 is a flow diagram illustrating generally use of the control system of FIG. 1.

Use of the control system 10 for controlling the surgical handpiece 14 is illustrated generally by the flow diagram of FIG. 2. With additional reference to FIG. 1, one preferred method of using the system 10 of the present invention begins at step 50 at which the controller 12 detects the presence of the surgical handpiece 14. For example, the powered surgical handpiece 14 can include a cord assembly 24 (not shown) terminating in a connector plug (not shown) that is otherwise connectable to a receiving port or socket (not shown) electrically connected to the controller 12. An example of an acceptable connection is provided in U.S. Pat. No. 5,903,117, the teachings of which are incorporated herein by reference. Alternative connection systems known in the art are equally acceptable, so long as the controller 12 is able to determine whether the surgical personnel have initiated a surgical procedure by selecting and connecting the handpiece 14. If, at step 50, the controller 12 does not defect the handpiece 14, operations do not continue.

Assuming the handpiece is properly connected, at step 52, the controller 12 determines whether the micro-cutting instrument 22 has been coupled to the handpiece 14, and the type of instrument. In this regard, the powered handpiece 14 can be configured to provide the controller 12 with a signal indicative of mounting of the micro-cutting instrument 22. Alternatively, surgical personnel may inform the controller 12 of the presence of the micro-cutting instrument 22 via the data entry device 16. In this regard, the controller 12 can receive information, either directly from the surgical handpiece 14 or from surgical personnel via the data entry device 16, indicative of the exact form the micro-cutting instrument 22. Alternatively, however, the system 10 does not require confirmation of the specific form of the micro-cutting instrument 22 to continue.

At step 54, the controller 12 generates information and operational characteristics associated with the particular surgical procedure to be performed. As described below, in a preferred embodiment, the controller 12 requests, via the display screen 18, surgical personnel to enter the particular procedure to be performed. For example, the surgical personnel can select, via the data entry device 16, a general anatomical location for the operation from a list generated by the controller 12 at the display screen 18. Additionally, or alternatively, the surgical personal can select a specific surgical procedures and corresponding anatomical location from a list generated by the controller 12 at the display screen 18. Even further, the controller 12 can have previously stored surgical procedure information that corresponds with the particular micro-cutting instrument 22 and/ or the particular handpiece 14 otherwise connected to the controller 12. With this configuration, the controller 12 selects appropriate procedural information from this database based upon the detected or sensed handpiece 14/micro-cutting instrument 22 information.

At step 56, the controller 12 causes the display screen 18 to display preferred operational settings based upon the generated surgical procedure information. For example, and as described below, the controller 12 signals the display screen 18 to display the preferred handpiece operational speed, the rotational mode, the fluid irrigation flow rate, and information identifying the surgical procedure for which the preferred settings relate. Upon reviewing the displayed information, the surgical personnel can confirm that the desired surgical procedure has been selected and can confirm the preferred operational settings. As a result, the surgical personnel are no longer required to separately investigate suggested settings, and, in one preferred embodiment, can rely upon the displayed values as default settings for the system 10.

At step 58, the controller 12 allows for operation of the powered surgical handpiece 14. For example, the surgeon can deploy the micro-cutting instrument 22 to the target site and initiate activation of the powered handpiece 14, for example via the speed controller 20. In response, and assuming that all previous steps have been properly performed, the controller 12 energizes the powered handpiece 14 such that the surgeon can complete the desired surgical procedure. In a preferred embodiment, the controller further activates and controls fluid flow from the irrigation fluid supply source 30 and the cooling fluid supply source 40 in accordance with desired operational parameters. As a point of reference, one example of controlled powering of a surgical handpiece is described in U.S. Pat. No. 5,903,117, the teachings of which are incorporated herein by reference. It should be understood, however, that a wide variety of other techniques for signaling, operating, and controlling a powered surgical handpiece, fluid sources, etc. via a controller are known in the art and are equally acceptable.

In a preferred embodiment, the controller 12 allows the surgeon (not shown) to control the speed of the powered surgical handpiece 14 via the speed controller 20. As previously described, the speed controller 20 is preferably a foot switch that is highly convenient for a surgeon's use. In a preferred embodiment, the controller 12 is configured to prevent operation of the handpiece 14 at speeds that would be inappropriate for the procedure being performed. For example, the controller can be provided with a lower limit and an upper limit speed value database specific to particular surgical procedures. When the surgeon attempts to operate the handpiece 14, for example, via the speed controller 20, above or below the limit values, the control system 12 prevents the handpiece 14 from being so-operated, for example by not signaling or otherwise energizing the handpiece 14 above or below the limiting values.

Figure 3:
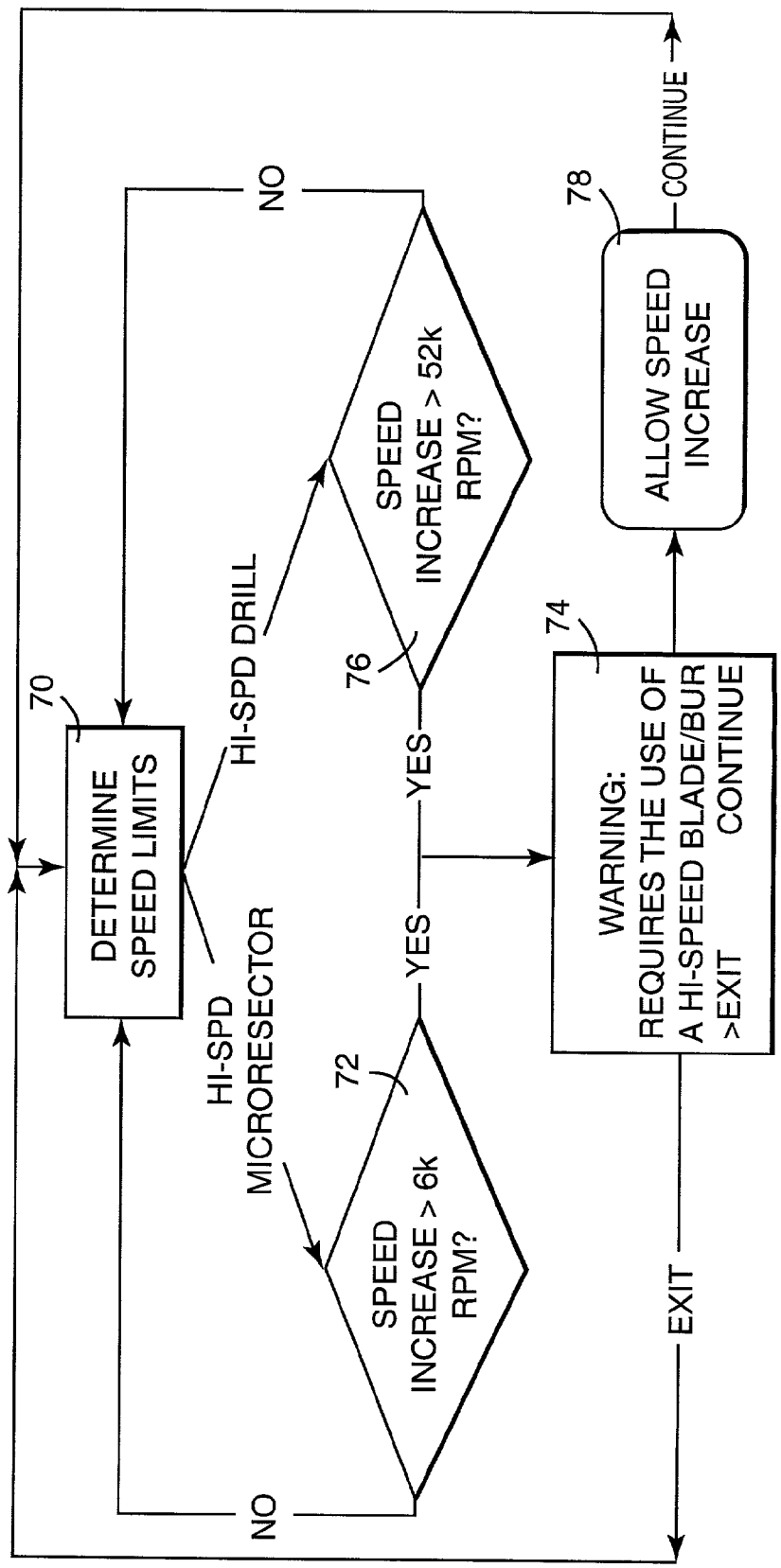
FIG. 3 is a flow diagram illustrating a warning operation performed by one preferred embodiment of the control system of FIG. 1.

Alternatively, the control system 10 can be configured to allow operation of the powered handpiece 14 above or below the pre-set limiting values, but provides the surgical personnel with a warning. For example, as shown by the flow diagram of FIG. 3, at step 70, the controller 12 determines whether the particular configuration of the handpiece 14 and the micro-cutting instrument 22 has a prescribed or preferred speed limit or range. As shown in FIG. 3, for example, the controller 12 includes a speed limit database containing limiting values for a micro-resector cutting instrument and a high-speed micro-drilling instrument. At step 72, the controller 12 determines that a micro-resecting instrument is being utilized as the micro-cutting instrument 22 and determines whether the surgeon is attempting to operate the powered handpiece 14 at speeds in excess of a pre-set value, for example, 6,000 rpm. If, at step 72, it is determined that the surgeon is not attempting to operate the handpiece 14 in excess of the preset value (or "no" at step 72), the method returns to step 70, and no warning is displayed.

Alternatively, if at step 72, the controller 12 determines that the surgeon is attempting to operate the powered handpiece 14 at speeds in excess of the preset limit, the method proceeds to step 74. A similar methodology is followed at step 76 relating to use of a high-speed micro-drill having a different present limit, for example 52,000 rpm.

Regardless, if the controller 12 determines, either at step 72 or step 76, that the surgeon is attempting to operate the handpiece 14 at a speed outside of the predetermined range, at step 74 the controller 12 causes the display screen 18 to display a warning to the surgical personnel, prevents the powered handpiece 14 from being operated at the requested speed (that is otherwise outside of the predetermined range) and requests information from the surgical personnel. For example, the warning associated with step 74 can indicate to the surgical personnel that a different micro-cutting instrument is better suited for the desired speed. Alternatively, other warnings can be provided.

If, at step 74, the surgical personnel chooses to not exceed the preselected speed range ("exit" at step 74), operation of the handpiece 14, via the controller 12 continues but at a level within the predetermined range, or the procedure can be stopped entirely so that a more appropriate micro-cutting instrument can be used. Alternatively, if the surgical personnel determines that the particular micro-cutting instrument 22 and the desired, non-conforming speed is appropriate ("continue" at step 74), the controller 12 proceeds to step 78 at which the controller 12 energizes the surgical handpiece 14 to the requested level.

Figure 4:
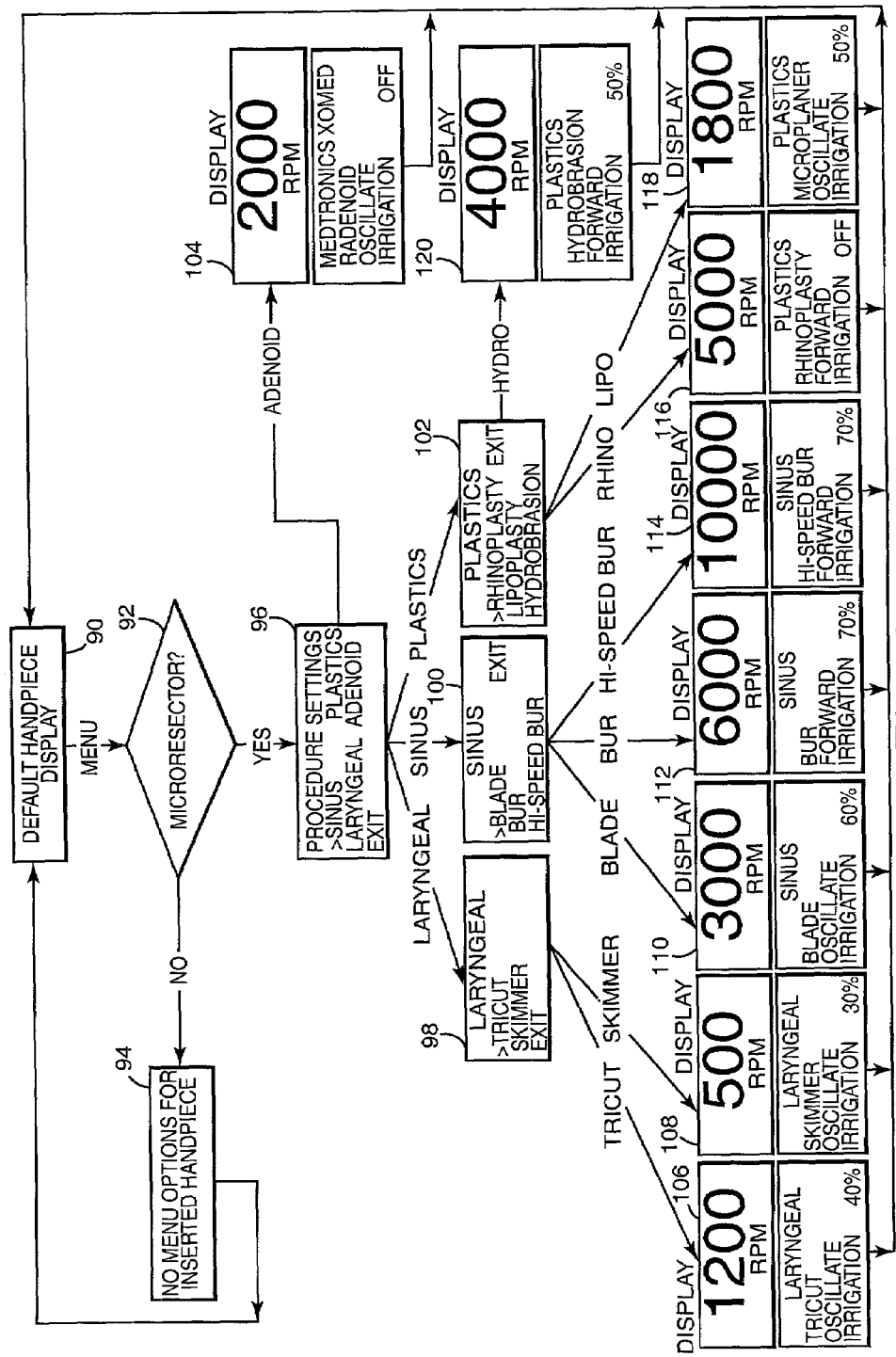
FIG. 4 is a flow diagram illustrating one specific application of the control system of FIG. 1.

One specific method of using the system 10 of the present invention is shown by the flow diagram of FIG. 4. Beginning at step 90, the controller 12 causes the display screen to display default information (for example, as described at step 54 in FIG. 2). At step 92, the controller 12 causes the display screen 18 to request information from the surgical personnel as to the specific form of the micro-cutting instrument 22. Alternatively, and as previously described, the powered handpiece 14 can be configured to directly signal this information to the controller 12. Once the type of cutting instrument is determined, the controller 12 determines whether its associated memory includes database information related to the micro-cutting instrument 22. If, at step 92, the controller 12 does not recognize the cutting instrument 22 ("no" at step 92), the control system 10 proceeds to step 94, and is unable to provide options to the surgical personnel. Conversely, where the controller 12 does recognize the particular cutting instrument 22, the control system 10 proceeds to step 96. By way of reference, the example provided in FIG. 4 relates to a micro-resector instrument.

At step 96, the controller 12 causes the display screen 18 to display a listing of anatomical regions or procedures for which the selected cutting instrument 22 is particularly adapted. For example, with respect to the micro-resector example of FIG. 4, the controller 12 will the cause the display screen 18 to display a listing of four anatomical regions including "sinus," "plastics" (or plastic surgery), "laryngeal," and "adenoid". In response, the surgical personnel select one of the listed procedures or anatomical regions via the data entry device 16.

Depending upon the selection made at step 96, the method proceeds to one of steps 98 (corresponding to "laryngeal" selection), step 100 (corresponding with "sinus" selection), step 102 (corresponding with "plastics" selection), or step 104 (corresponding with "adenoid" selection).

Assuming, for example, that laryngeal is selected, and thus that the method has proceeded to step 98, the controller 12 causes the display screen 18 to display additional procedural requests. For example, a listing of "tricut" and "skimmer" can be displayed. In response, the surgical personnel must select, via the data entry device 16, one of the displayed procedures.

Assuming, for example, that the surgical personnel selects "tricut" at step 98, the method proceeds to step 106 at which the controller 12 causes the display screen 18 to display preferred operational parameters associated with the selected procedure. For example, and as shown in the FIG. 5, at step 106 the display screen 18 displays a preferred rotational speed (i.e., 1,200 rpm), the selected surgical procedure (i.e., laryngeal tricut), the operational mode (i.e., oscillate), and the irrigation settings (i.e., 40%). Based upon this display, then, the surgical personnel can easily and clearly identify the preferred operational parameters, and can confirm that the information corresponds with the desired procedure. Similar displays are provided for other specifically selected procedures (i.e., indicated general at steps 104 and 108–120). Obviously, the displays illustrated in FIG. 5 are but a few examples of acceptable formatting and information.

Figure 5:
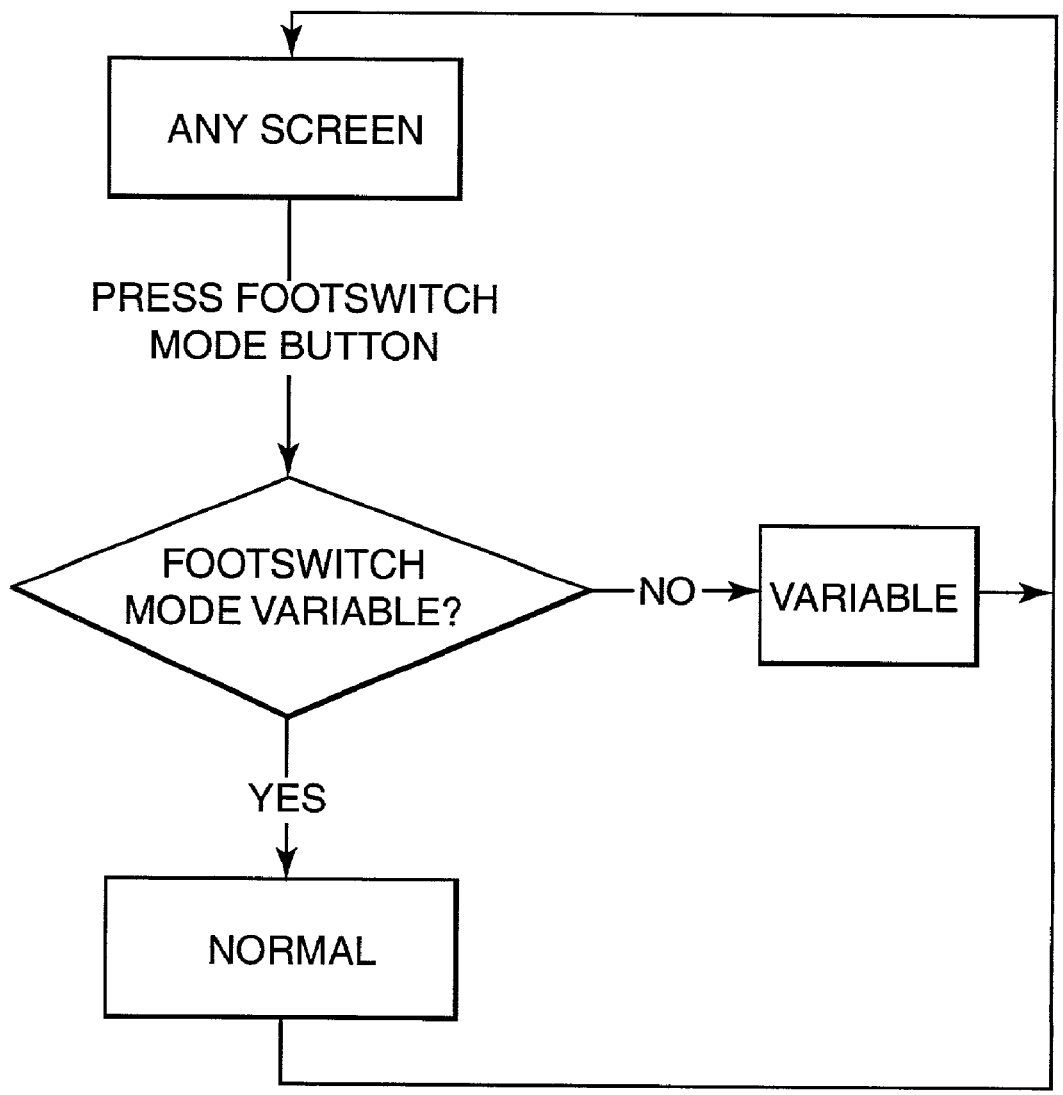
FIG. 5 is a flow diagram illustrating a speed control feature associated with one preferred embodiment of the control system of FIG. 1.
Figure 6:
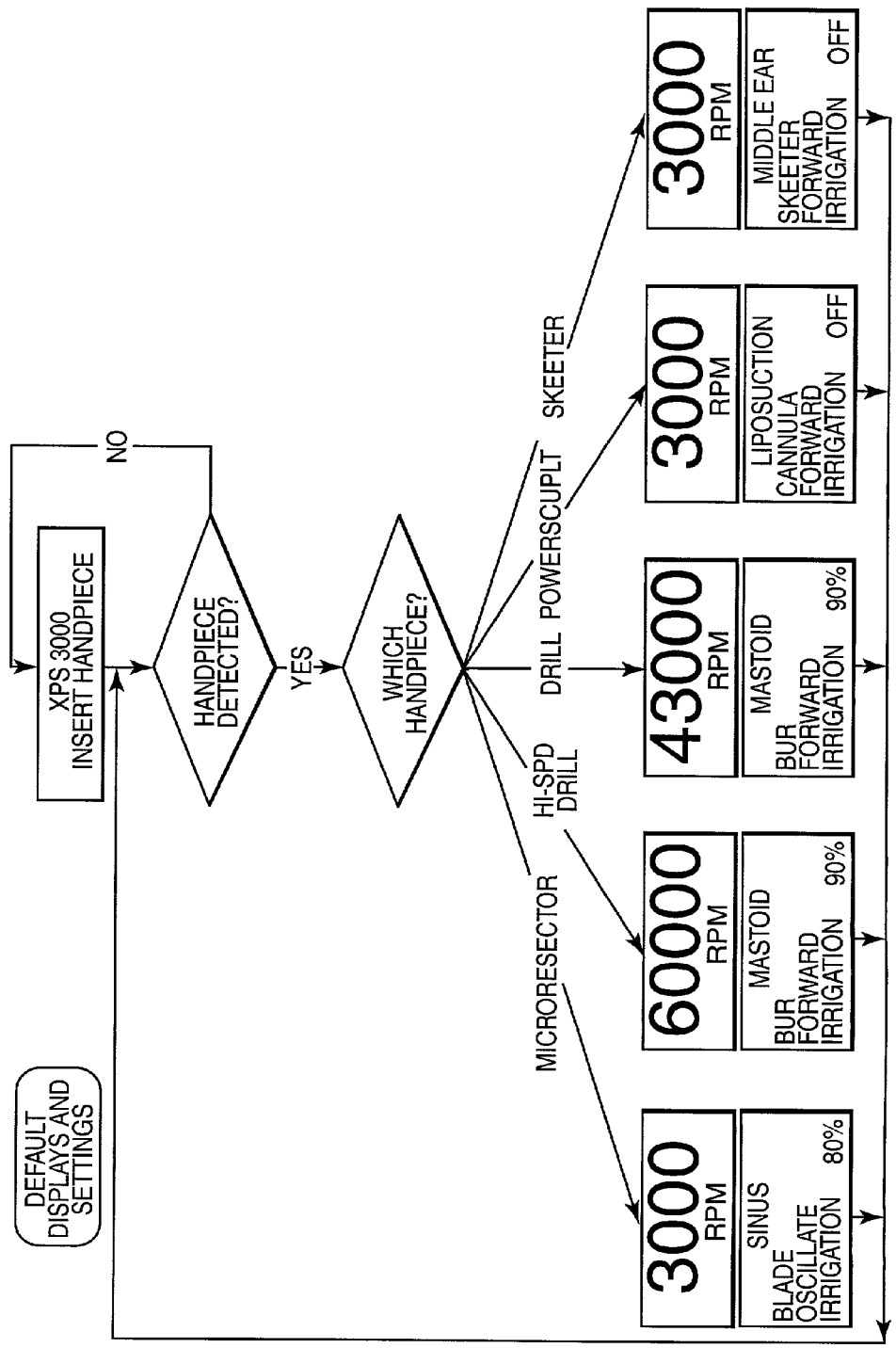
FIG. 6 is flow diagram illustrating an application of the control system of FIG. 1.

An additional operational feature or method associated with the control system 10 of the present invention is provided in FIG. 5, whereby the controller 12 confirms preferred operation of the speed controller 20 in either normal, such as "Start/Stop," or variable mode.

In one alternative embodiment, the control system 10 is configured for use with an image guidance system. Image guidance systems are well known in the art, and rely upon stereotactic techniques to assist surgeons in performing operations in or near the head. One example of an acceptable image guidance system is available under the trade name LandmarX from Medtronic-Xomed of Jacksonville, Fla. Regardless of the exact configuration, the image guidance system includes a high-definition screen that displays the patient's internal anatomy along with a relative position of the particular instrument being employed as part of the surgical procedure. Due to the highly delicate nature of these procedures, the surgeon is required to constantly view the image guidance system display screen. With this in mind, and in the alternative embodiment, the control system 10 is configured such that the controller 12 is directly connected to the image guidance system display screen. Any display generated by the controller 12 relating to operational parameters of the surgical handpiece 14 are offset from or otherwise positioned so as to not interfere with viewing of the image guidance system display. However, by providing the operational parameters display as part of, or immediately adjacent to, the image guidance system display, the surgeon can check the operating conditions for the handpiece continuously as the device is operating without diverting his or her attention away from the screen otherwise showing the position of the tool relative to the patient's anatomy.

The powered surgical handpiece control system and related method of the present invention provides a marked improvement over previous designs. In particular, regardless of the exact surgical procedure and related micro-cutting instrument, the surgical personnel are immediately provided with preferred operational parameters. The control system preferably prevents the surgeon from inadvertently deviating from the generated operational parameters, and provides a simple user interface specific to ENT/head/neck procedures.

What is claimed is:

1. A motor control system for a powered surgical handpiece capable of powering various micro-cutting instruments, the system comprising:
   a controller programmed for selective electronic connection to a powered surgical handpiece and for controlling the powered surgical handpiece based upon user-defined procedural information, the controller including a database storing prescribed operational ranges for a plurality of micro-cutting instruments useful with the powered surgical handpiece, wherein the controller is further adapted to:
   identify a micro-cutting instrument coupled to the powered surgical handpiece, and
   signal when a user is attempting to operate the identified micro-cutting instrument outside the prescribed operational range corresponding to the identified micro-cutting instrument; and
   a data entry device for entering the user-defined procedural information to the controller.

2. The system of claim 1, wherein the identified micro-cutting instrument is a first micro-cutting instrument, and the controller is adapted to generate user feedback information including a suggestion of a second micro-cutting instrument suited for use outside the prescribed operational range corresponding to the first micro-cutting instrument.

3. The system of claim 2, wherein the controller suggests the second micro-cutting instrument based on a second prescribed operational range corresponding to the second micro-cutting instrument.

4. The system of claim 2, further comprising a display device adapted to communicate the suggestion to use the second micro-cutting instrument in response to a prompt from the controller.

5. The system of claim 1, wherein the user-defined procedural information includes a procedure to be performed and an anatomical location where the procedure will be performed.

6. The system of claim 1, wherein the controller includes an operational limit database containing pre-set limiting values of at least one operational performance parameter for each of a plurality of procedures, and the data entry device is adapted to allow a user to indicate a selection of one of the plurality of procedures.

7. The system of claim 6, wherein the controller is adapted to signal when a user is attempting to operate the identified micro-cutting instrument outside the pre-set limiting values corresponding to the selected one of the plurality of procedures.

8. The system of claim 1, wherein the controller is additionally adapted to select procedural information from the database based on the identified micro-cutting instrument.

9. The system of claim 8, wherein procedural information is for a plurality of procedures associated with the identified micro-cutting instrument, and the data entry device is adapted to allow a user to indicate a selection of one of the plurality of procedures associated with the identified micro-cutting instrument.

10. The system of claim 1, further comprising a display screen electrically connected to the controller, wherein the controller is adapted to prompt the display screen to present a list of anatomical regions for which the identified micro-cutting instrument is adapted for use in surgery thereon.

11. The system of claim 10, wherein the data entry device is adapted to receive a user-selected anatomical region selected from the list of anatomical regions, and wherein the controller is adapted to determine a list of procedures associated with the micro-cutting instrument and the user-selected anatomical region.

12. The system of claim 11, wherein the data entry device is adapted to receive a user-selected procedure selected from the list of procedures, and the controller is adapted to access the pre-set limiting values from the database corresponding to the user-selected procedure.

13. The system of claim 12, wherein the controller is configured to compare pre-set limiting values corresponding to the user-selected procedure and to signal when the user is attempting to operate the identified micro-cutting instrument outside the pre-set limiting values corresponding to the user-selected procedure.

14. The system of claim 1, wherein the controller is adapted to prevent operation of the micro-cutting instrument outside the operational range corresponding to the identified micro-cutting instrument.

15. The system of claim 1, wherein the prescribed operational range includes a prescribed speed range.

16. The system of claim 1, wherein the controller is adapted to provide pre-set limiting values of at least one operational performance parameter based on the identified micro-cutting instrument and the user-defined procedural information.

17. The system of claim 16, wherein the controller is adapted to monitor powering of the powered surgical handpiece pursuant to the pre-set limiting values and the prescribed operational range corresponding with the identified micro-cutting instrument.

18. The system of claim 16, further comprising a display device electronically connected to the controller for displaying the selected pre-set limiting values of the at least one operational performance parameter.

19. The system of claim 1, further comprising a display screen in communication with the controller, wherein the controller is adapted to interpret the user-defined procedural information and request additional information from a user via the display screen to determine the system configuration, and further wherein the controller is adapted to control energization of the handpiece according to the user-defined procedural information.

* * * * *